United States Patent [19]

D'Silva

[11] 4,156,731

[45] May 29, 1979

[54] HETEROCYCLIC OXIME COMPOUNDS AND CARBAMOYLOXIME DERIVATIVES

[75] Inventor: Themistocles D. J. D'Silva, South Charleston, W. Va.

[73] Assignee: Union Carbide Corporation, New York, N.Y.

[21] Appl. No.: 727,935

[22] Filed: Sep. 29, 1976

[51] Int. Cl.$^2$ .................... A61K 31/38; C07D 333/22
[52] U.S. Cl. .............................. 424/277; 424/248.51; 260/327 M; 544/145
[58] Field of Search .................... 260/327 M, 247.1 P; 424/277, 248; 544/145

[56] References Cited

U.S. PATENT DOCUMENTS

| | | | |
|---|---|---|---|
| 2,690,988 | 10/1954 | Jones et al. | 260/327 M |
| 3,183,148 | 5/1965 | Cannon et al. | 167/33 |
| 3,639,471 | 2/1972 | Klauke et al. | 260/544 C |
| 3,681,386 | 8/1972 | Fridinger et al. | 260/327 M |
| 3,956,500 | 5/1976 | Durden et al. | 424/276 |
| 3,992,549 | 11/1976 | Durden et al. | 424/277 |

OTHER PUBLICATIONS

Jensen et al., Acta Chem. Scand., vol. 22, pp. 1107–1128 (1968).
Oglobin et al., J. Gen. Chem., USSR, vol. 34, pp. 1227 to 1234 (1964).
Hackh's Chemical Dictionary, 4th Ed. (McGraw-Hill, N.Y., 1969) pp. 320–321.

*Primary Examiner*—John D. Randolph
*Attorney, Agent, or Firm*—Robert C. Brown

[57] ABSTRACT

Heterocyclic oxime compounds are useful as intermediates in the preparation of pesticidally active carbamoyloxime compounds.

88 Claims, No Drawings

HETEROCYCLIC OXIME COMPOUNDS AND CARBAMOYLOXIME DERIVATIVES

This invention relates to 4-oximino-1,3-dithiolane oxime and 4-carbamoyloximino-1,3-dithiolane carbamate compounds and to their preparation. This invention is also directed to insecticidal and miticidal compositions comprising an acceptable carrier and an insecticidally and miticidally effective amount of a carbamate compound of this invention as well as to a method of controlling insects and mites by subjecting them to an insecticidally or miticidally effective amount of a carbamate compound of this invention.

More particularly, this invention relates to compounds of the formula:

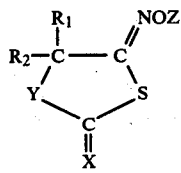

wherein:

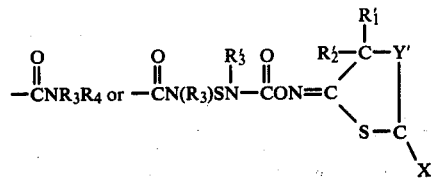

Z is hydrogen, $R'_1$, $R'_2$, $R_1$ and $R_2$ are individually hydrogen or alkyl;

$R_3$ and $R_4$ are individually hydrogen or alkyl or when $R_3$ is alkyl, $R_4$ may also be alkanoyl, haloalkanoyl, trihalomethanosulfenyl, tetrahaloethanesulfenyl, dialkylaminosulfenyl, heterocyclicaminosulfenyl, or either unsubstituted or substituted alkylsulfenyl, phenylsulfenyl, cycloalkylsulfenyl, alkylthiosulfenyl, cycloalkylthiosulfenyl or phenylthiosulfenyl wherein the permissible substituents are one or more fluoro, chloro, bromo, cyano, nitro, alkyl, alkanoyl, alkoxy, phenyl, phenoxy, trihalomethyl or aroyl substituents in any combination.

$R'_3$ is alkyl;

$Y'$ and $Y$ are individually sulfur, sulfinyl or sulfonyl;

$X'$ and $X$ are individually sulfur

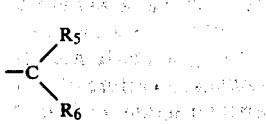

or —N—$R_7$ wherein $R_5$ and $R_6$ are individually hydrogen, alkyl, alkanoyl, alkoxycarbonyl, nitro, cyano or either substituted or unsubstituted phenyl wherein the permissible substituents are from 1 to 3 fluoro, chloro, cyano, nitro or trihalomethyl substituents in any combination; with the proviso that both $R_5$ and $R_6$ may not be hydrogen, alkyl or phenyl;

$R_7$ is alkyl, alkylsulfonyl, cycloalkyl, cyano, dialkylamino or either substituted or unsubstituted phenyl, phenylamino or phenylsulfonyl wherein the permissible substituents are from 1 to 3 fluoro, chloro, cyano, nitro or trihalomethyl substituents in any combination.

In general, $R_1$, $R'_1$, $R'_2$, $R_2$, $R'_3$, $R_3$, $R_4$, $R_5$, $R_6$ and $R_7$ substituents individually may not include more than eight aliphatic carbon atoms. Preferred either because of their higher level of insecticidal and miticidal activity or because of their usefulness as intermediates in the preparation of carbamate compounds that exhibit outstanding pesticidal activity are the compounds of this invention in which $R_1$ and $R_2$ are individually hydrogen or alkyl having from 1 to 4 carbon atoms and $R_3$ is methyl.

The carbamate compounds of this invention are those of the above formula in which

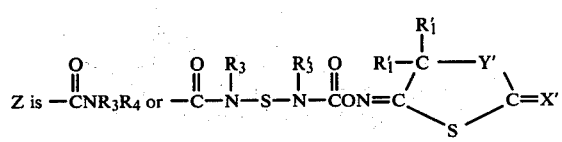

and $Y'$, $Y$, $X'$, $X$, $R'_1$, $R_1$, $R'_2$, $R_2$, $R'_3$, $R_3$, $R_4$, $R_5$, $R_6$ and $R_7$ are described above. These compounds exhibit outstanding miticidal and insecticidal activity and may be used as miticides and insecticides utilizing those methods known to those skilled in the pesticidal art. They are also relatively non-toxic to plants and mammals when used in amounts sufficient to kill insects and mites.

The oxime compounds of this invention are those of the above formula in which Z is hydrogen and $R_1$, $R_2$, $X$, $Y$, $R_5$, $R_6$ and $R_7$ are as described above. These compounds are useful as intermediates in the preparation of the insecticidally and miticidally active carbamate compounds. An oxime compound of this invention can be reacted with an appropriately substituted carbamoyl halide compound in the presence of a suitable acid acceptor to produce the corresponding carbamate compound. For example, 5,5-dimethyl-2-dimethylhydrazono-4-oximino-1,3-dithiolane can be reacted with N-methyl-N-(4-(tert-butyl)phenylthiosulfenyl) carbamoyl fluoride in the presence of triethylamine as an acid acceptor, to produce 5,5-dimethyl-2(N,N-dimethyl-hydroazono)-4-[[O-[N-methyl-N-[4-(tert-butyl)phenylthiosulfenyl)carbamoyl]oximino]]-1,3-dithiolane, the corresponding insecticidally and miticidally active carbamate compound. The oxime compounds of this invention can also be reacted with other chemical species containing electron deficient reaction sites, such as isocyanate compounds or phosgene followed by reaction with an appropriately substituted amine, to produce insecticidally and miticidally active carbamate compounds. The above disclosed reactions are described in more detail below.

The compounds of this invention can be prepared in accordance with a variety of methods. Two preferred methods for preparing the oxime compounds of this invention are illustrated by the general reaction schemes set forth below in which X, $R_1$, $R_2$, $R_5$, $R_6$ and $R_7$ are as described above and M is an alkali metal cation.

METHOD I

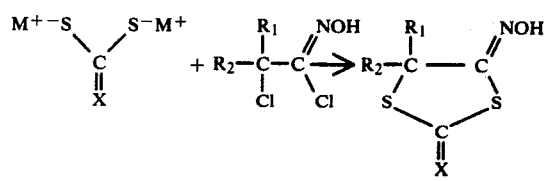

METHOD II

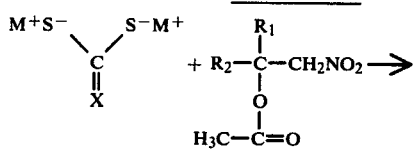

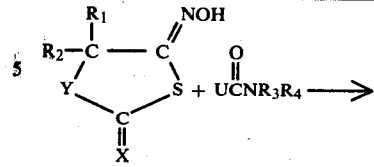

METHOD V

METHOD VI

The carbamate and bis-carbamate compounds of this invention can be prepared by a variety of methods which utilize the oxime compounds of this invention as precursors. Four preferred methods are illustrated by the reaction schemes set forth below in which $R_1$, $R'_1$, $R'_2$, $R_2$, $R'_3$, $R_3$, $R_4$, $R_5$, $R_6$, $R_7$, $Y'$, $X'$, $X$ and $Y$ are as described above and U is chlorine or fluorine, except as noted:

METHOD III

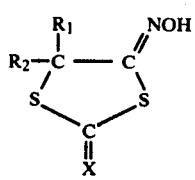

In Method III, $R_3$ is alkyl.

METHOD IV

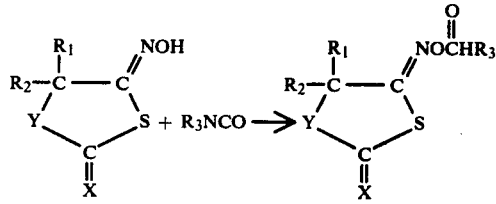

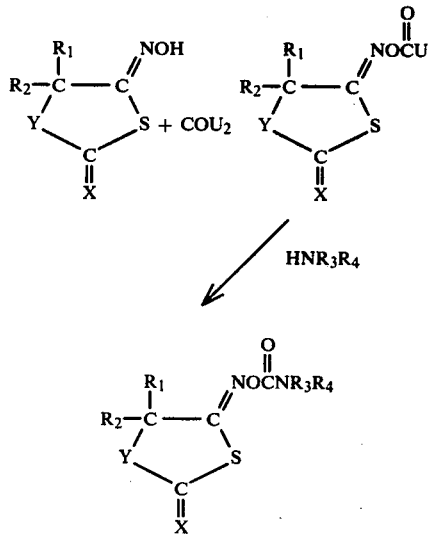

In Method IV, $R_3$ and $R_4$ are individually hydrogen or alkyl.

The reactions of Methods I and II can be conducted in organic solvents, in an aqueous solvent or in a two-phase mixture of organic and aqueous solvents. Illustrative of organic useful in the conduct of these reactions are methanol, ethanol, xylene, methylene chloride or the like. These reactions are preferably carried out in either an aqueous solvent or in an aqueous/alcoholic solvent mixture.

The reactions illustrated in Methods III, IV, V and VI are conducted in inert solvents. Any inert solvent such as benzene, toluene, xylene, dioxane, tetrahydrofuran or the like can be used in these reactions.

Reaction temperatures are not critical and can be varied over a wide range depending to a large extent on the reactivity and the stability of the reactants. The reactions of Methods I and II are preferably conducted at a temperature of from about $-20°$ C. to about $50°$ C. The reactions of Methods III, IV, V and VI are preferably conducted at a temperature of from about $-30°$ C. to about $100°$ C. Reaction pressures are not critical. For convenience these reactions are usually conducted at atmospheric or autogeneous pressure.

The reaction illustrated in Method III is preferably conducted in the presence of a quantity of a catalyst sufficient to provide a suitable and reasonable reaction rate. In general, any conventional catalyst of the type commonly employed to promote reactions between isocyanate compounds and compounds that contain an active hydrogen can be used. Illustrative of materials useful as catalyst in the conduct of this reaction are organic bases such as organic amines, alkali metal alkoxides, alkali metal alkylides or the like and inorganic bases such as alkaline earth hydroxides, alkali metal hydroxides and the like. Organic and inorganic acids may also be used as catalyst in this reaction. Preferred catalyst are tertiary amines such as triethylamine, trimethylamine, pyridine or the like and dibutyltin diacetate.

The reactions illustrated in Methods IV, V and VI are conducted in the presence of an acid acceptor. The molar ratio of said acceptor to either reactant is substantially equimolar although a slight excess of acid acceptor may be employed if desired. The acid acceptor employed is a basic material which may be either an organic or an inorganic base. Illustrative of organic bases which are useful as acid acceptors in these reactions are tertiary amines, alkali metal alkoxides or the like. Bases such as potassium hydroxide, sodium hydroxide or the like are illustrative of inorganic bases that can be used as acid acceptors in the conduct of these reactions. Tertiary amines such as trimethylamine, triethylamine, pyridine or 1,4-diazabicyclo[2.2.2] octane and alkali metal hydroxides, such as sodium or potassium hydroxide are preferred acid acceptors in these reactions.

The reactions of Methods V and VI can be conducted either when an inorganic base is employed as an acid acceptor in a homogeneous phase system or a heterogeneous phase system. In the latter case phase transfer agents such as a crown ether compound, quaternary ammonium halide compound or the like, may be used to facilitate the transfer of the reactants across the phase interface. For example, when an inorganic base is employed as an acid acceptor in an organic solvent medium a crown ether compound may be used as the phase transfer agent or, alternatively, when these reactions are conducted in a two-solvent phase system, which consists of an aqueous solution of an inorganic base acid acceptor as one phase and an organic solvent containing dissolved reactants as the other phase, a quaternary ammonium salt may be employed as the phase transfer agent.

The carbamate compounds of this invention in which $R_4$ is alkanoyl can be prepared by reacting the corresponding carbamate compound in which $R_4$ is hydrogen with an appropriately substituted alkanoyl halide or an anhydride, or, alternatively by the reaction illustrated in Method IV wherein $R_4$ is an alkanoyl function.

The compounds of this invention wherein Y and/or Y' are individually sulfinyl or sulfonyl can be prepared by the oxidation of the corresponding compound in which Y and/or Y' is sulfur with an oxidizing agent, such as peroxy acids, at an appropriate point in the synthetic procedure.

The dithiolate compounds utilized as reactants in the reaction of Methods I and II can be prepared as described in U.S. Pat. No. 3,915,962, K. A. Jensen, et al Acta. Chem. Scand. 22, 1107 (1968) and references cited therein. The 2-chlorohydroxamoyl chloride compounds reactants of Method I can be prepared by the method described in Ogloblin et al, J. Gen. Chem. USSR, 34, 1225 (1964), and the nitro alkylacetate compounds utilized as reactants in Method II can be prepared by the acetylation of the corresponding nitroalkyl alcohol.

2-Oximino-1,3-dithiolane compounds utilized as reactants in the reactions illustrated in Methods III, IV, V and VI can be prepared as described hereinabove. Isocyanate, carbonyl chloride, carbonyl fluoride and amine compounds employed as reactants in these reactions are well known compounds that can be either obtained from commercial sources or prepared in accordance with methods well known to those skilled in the synthetic art.

Carbamoyl halide compounds utilized as reactants in the reaction illustrated in Method V can be prepared in accordance with a variety of conventional methods. The choice of method is influenced to a large extent by $R_4$ substituent patterns. For example the preferred methods of preparing carbamoyl fluoride reactants in which $R_4$ is either a substituted sulfenyl substituent, a substituted aminosulfenyl substituent or a substituted thiosulfenyl substituent is by reacting hydrogen fluoride with an appropriately substituted isocyanate to form the monosubstituted carbamoyl fluoride which is then reacted with an appropriately substituted sulfenyl, or thiosulfenyl chloride compound in the presence of an acid acceptor to form the corresponding N-sulfenylated, N-aminosulfenylated or N-thiosulfenylated carbamoyl fluoride compound respectively. For example, hydrogen fluoride can be reacted with methyl isocyanate dissolved in toluene to produce N-methylcarbamoyl fluoride which, in turn, can be reacted with p-tert-butylphenylsulfenyl chloride, in the presence of essentially an equivalent amount of triethylamine, to produce N-methyl-N-(4-tert-butylphenylsulfenyl)carbamoyl fluoride. This procedure is described in more detail in U.S. Pat. No. 3,639,471. One preferred method of preparing carbamoyl halide reactants in which $R_3$ and/or $R_4$ are bonded to nitrogen through a carbon nitrogen bond is by reacting an appropriately substituted amine with a carbonyl halide, such as phosgene, in the presence of an acid acceptor as for example triethylamine.

4-[O-[N-Alkyl-N-(N'-alkyl-N'-fluorocarbonylaminosulfenyl)carbamoyl]oximino]-1,3-dithiolane reactants of Method VI can be conveniently prepared by reacting hydrogen fluoride with an alkyl isocyanate to form N-alkyl carbamoyl fluoride compound which is then reacted with sulfur dichloride ($SCl_2$) to form the bis-(N-alkyl-N-fluorocarbonylamino)sulfide compound which may then be reacted with an equivalent amount of an appropriately substituted 4-oximino-1,3-dithiolane compound.

The following specific examples are presented to more particularly illustrate this invention.

EXAMPLE I

Preparation of Dipotassium dicyanoethylidene dithiolate (A)

To a suspension of 44.8 grams (0.8m) of pulverized potassium hydroxide in 700 ml of dioxane, cooled to 15° C., was added dropwise a solution of 26.4 grams (0.4m) of malononitrile and 30.4 grams (0.4m) of carbon disulfide dissolved in 100 ml of dioxane. After the addition was completed, the mixture was stirred for 0.5 hours and the solid formed was filtered, washed with ether, and dried to afford 80.5 grams of the dithiolate salt.

The compounds of Examples II-XVIII listed in Table I below were prepared by reacting compounds with active methylenes, primary amines or carbon disulfide with an alkali metal hydroxide as described more fully in Example I.

TABLE I

| Example | Formula of Dithiolate | Starting methylene Compound or Amine | Alkali Metal Hydroxide |
|---|---|---|---|
| II | $(NC)_2C=C(SK)_2$ | Malononitrile | KOH |
| III | $C_2H_5CO_2(CN)C=C(SK)_2$ | Ethylcyanoacetate | KOH |
| IV | $Ph(CN)C=C(SK)_2$ | Phenylacetonitrile | KOH |
| V | $H(NO_2)C=C(SK)_2$ | Nitromethane | KOH |
| VI | $H(COCH_3)C=C(SK)_2$ | Acetone | KOH |
| VII | $NCN=C(SK)_2$ | Cyanamide | KOH |
| VIII | $CH_3N=C(SK)_2$ | Methylamine | KOH |
| IX | $C_2H_5N=C(SK)_2$ | Ethylamine | KOH |
| X | $i\text{-}C_3H_7N=C(SK)_2$ | Isopropylamine | KOH |
| XI | $t\text{-}C_4H_9N=C(SK)_2$ | Tert-Butylamine | KOH |
| XII | $C_4H_9N=C(SK)_2$ | Butylamine | KOH |
| XIII | $cyclo\text{-}C_6H_{11}N=C(SK)_2$ | Cyclohexylamine | KOH |
| XIV | $(CH_3)_2N-N=C(SK)_2$ | N,N-Dimethylhydrazine | KOH |
| XV | $CH_3SO_2N=C(SK)_2$ | Methanesulfonamide | KOH |
| XVI | $CH_3\text{-}\langle\text{phenyl}\rangle\text{-}SO_2N=C(SK)_2$ | p-Toluenesulfonamide | KOH |
| XVII | $Cl\text{-}\langle\text{phenyl(CH}_3\text{)}\rangle\text{-}N=C(SK)_2$ | 4-chloro-2-methylaniline | KOH |
| XVIII | $S=C(SNa)_2$ | — | NaOH |

EXAMPLE XIX

Preparation of 5,5-Dimethyl-2-(cyanoethoxycarbonylmethylidene)-4-oximino-1,3-dithiolane. (Method I)

To a solution of 26.5 grams (0.1m) of dithiolate salt (III) in 300 ml of water, cooled to 5° C., was added with stirring a solution of 15.6 grams (0.1m) of 2-chloro-2-methylpropionohydroxamoyl chloride dissolved in 20 ml of ethanol. The yellow precipitate turned into a soft solid mass. After stirring for 0.5 hours, the liquid was decanted and discarded. On crystallization from benzene petroleum ether solution it afforded 11.0 grams of a crystalline material. m.p. 148°–150° C.

Infra-red (KBr) 3.08 (broad) OH; 4.52 (CN); 5.92 (C=O); 6.15 (C=N)μ.

The NMR was consistent with the proposed structure.

EXAMPLE XX

Preparation of 5,5-Dimethyl-2-isopropylimino-4-oximino-1,3-dithiolane. (Method I).

To a solution of 4.23 grams (0.02m) of the isopropylimino dithiolate salt (X) in 75 ml of water and 5 ml of ethanol was added dropwise with stirring at 5°–10° C., 3.12 grams (0.02m) of 2-chloro-2-methylpropionohydroxamoyl chloride over a period of 5 minutes. Some amorphous solid precipitated and the solution was acidic to pH test paper. An additional 4.0 grams of the dithiolate salt (X) was added until the reaction mixture was neutral. The solid formed was filtered and recrystallized from pentane-isopropyl ether solution to afford 2.0 grams of the product. m.p. 116°–118° C.

EXAMPLE XXI

Preparation of 2-(2-Oxopropylidene)-4-oximino-1,3-dithiolane (Method II).

To a solution of 6.8 grams (0.5m) of 4,4-dimercapto-3-buten-2-one in ethanol cooled to 10° C. was added 2.0 grams (0.5m) of sodium hydroxide dissolved in 30 ml of ethanol followed by dropwise addition at 0°–10° C. of 6.7 grams (0.5m) of nitroethylacetate dissolved in ethanol.

The solid was filtered and the filtrate concentrated to a residual oil. The filtered solid and the residual oil were mixed and taken in ethylacetate. It was washed with water, dried over magnesium sulfate, and concentrated to a light brown solid. Weight of the product: 4.6 grams. Recrystallized from isopropylether-benzenemethylene chloride to afford a light yellow solid. m.p. 175°–177° C.

The compound of EXAMPLES XXII–XXXIX were prepared using the methods of EXAMPLES XIX–XXI. Their physical properties are listed in TABLE II below.

TABLE II

MELTING POINTS AND NMR CHEMICAL SHIFTS OF 4-OXIMINO-1,3-DITHIOLANES

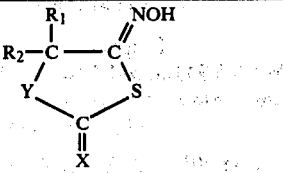

| Example | $R_1$ | $R_2$ | X | Y | m.p., °C. |
|---|---|---|---|---|---|
| XXII | $CH_3$ | $CH_3$ | $N-CH_3$ | Sulfur | 95–110 |
| XXIII | $CH_3$ | $CH_3$ | $N-CH_2CH_3$ | Sulfur | 126–128 |
| XXIV | $CH_3$ | $CH_3$ | $N-CH(CH_3)_2$ | Sulfur | 116–118 |
| XXV | $CH_3$ | $CH_3$ | $N-C(CH_3)_3$ | Sulfur | 150–152 |
| XXVI | $CH_3$ | $CH_3$ | $N$-n-$C_4H_9$ | Sulfur | 44–48 |
| XXVII | $CH_3$ | $CH_3$ | $N-N(CH_3)_2$ | Sulfur | 138–141 |
| XXVIII | $CH_3$ | $CH_3$ | cyclo-$C_6H_{11}-N$ | Sulfur | Oil |
| XXIX | $CH_3$ | $CH_3$ | $CH_3-C_6H_4-SO_2-N$ | Sulfur | 130–142 |
| XXX | $CH_3$ | $CH_3$ | $CH_3SO_2-N$ | Sulfur | 65–87 |
| XXXI | $CH_3$ | $CH_3$ | $N-C\equiv N$ | Sulfur | 182–184 |
| XXXII | $CH_3$ | $CH_3$ | $NCH_3$ | Sulfinyl | 124–125 |
| XXXIII | $CH_3$ | $CH_3$ | S | Sulfur | 85–100 |
| XXXIV | $CH_3$ | $CH_3$ | $C_2H_5CO_2(CN)C-$ | Sulfur | 148–150 |
| XXXV | $CH_3$ | $CH_3$ | $(CN)_2C-$ | Sulfur | 179–182 |
| XXXVI | $CH_3$ | $CH_3$ | $Ph(CN)C-$ | Sulfur | Oil |
| XXXVII | $CH_3$ | $CH_3$ | $H(NO_2)C$ | Sulfur | 184–188 |
| XXXVIII | $CH_3$ | $CH_3$ | $H(COCH_3)C-$ | Sulfur | 165–167 |
| XXXIX | H | H | $H(COCH_3)C-$ | Sulfur | 175–177 |

EXAMPLE XL

Preparation of 5,5-Dimethyl-2-methylimino-4-[O-(N-methylcarbamoyl)oximino]-1,3-dithiolane. (Method III)

To a solution of 2.0 grams (0.0084m) of 5,5-dimethyl-2-methylimino-1,3-dithiolane (XXII) in 50 ml of acetonitrile, taken in a pyrex pressure bottle, was added 0.75 ml of methyl isocyanate and 5 drops of triethylamine. After standing for 16 hours the reaction mixture was concentrated to an oil and purified by chromatography over silica gel to afford 1.6 grams of the product. m.p. 68°–70° C.

Calc'd for $C_8H_{13}N_3O_2S_2$: C, 38.85; H, 5.29; N, 16.99. Found: C, 38.79; H, 5.30; N, 16.90.

EXAMPLE XLI

Preparation of 5,5-Dimethyl-2-ethylimino-4-[[O-[N-methyl-N-(trichloromethanesulfenyl)carbamoyl]oximino]]-1,3-dithiolane (Method V)

To a solution of 3.5 grams (0.017m) of 5,5-dimethyl-2-ethylimino-4-oximino-1,3-dithiolane (XXIII) and 3.84 grams (0.017m) of N-methyl-N-trichloromethanesulfenyl carbamoyl fluoride in 75 ml of dioxane, was added dropwise with stirring 1.71 grams (0.017m) of triethylamine. After allowing the reaction mixture to stand at room temperature for 16 hours it was diluted with 250 ml of cold water and was extracted in ethylacetate. The organic extract was washed with water, dried over magnesium sulfate and concentrated under reduced pressure to a residual oil which crystallized on the addition of isopropyl ether and hexane, to afford 4.0 grams of a white solid. m.p. 69°–71° C.

Calc'd for $C_{10}H_{14}Cl_3N_3O_2S_3$: C, 29.24; H, 3.43; N, 10.23. Found: C, 29.61; H, 3.46; N, 10.30

EXAMPLE XLII

Preparation of 5,5-Dimethyl-2-(N',N'-dimethylhydrazono)-4-[[O-[N-methyl-N-tert-butylthiosulfenyl)carbamoyl]oximino]]-1,3-dithiolane (Method V)

To a solution of 1.8 grams (0.008m) of 5,5-dimethyl-2-dimethyl-hydrazono-4-oximino-1,3-dithiolane (XXVII) in 25 ml of dioxane was added 1.59 grams (0.008m) of N-methyl-N-(tert-butylthiosulfenyl)carbamoyl fluoride, followed by dropwise addition of 1.81 g (0.008m) of triethylamine. After stirring for 48 hours, at room temperature, the reaction mixture was diluted with 200 ml of cold water and the product was isolated in ethylacetate. The organic extract was washed with water, was dried over magnesium sulfate and concentrated to 2.1 grams of a residual oil. Purification through a silica gel column gave 1.2 grams of the pure material as an oil.

Calc'd for $C_{13}H_{24}N_4O_2S_4$: C, 39.36; H, 6.10; N, 14.12. Found: C, 38.79; H, 5.68; N, 13.26.

EXAMPLE XLIII

Preparation of 5,5-Dimethyl-2-(dicyanomethylidene)-4-[O-(N,N-dimethylcarbamoyl)oximino]-1,3-dithiolane (Method IV)

A solution of 4.0 grams (0.018m) of 5,5-dimethyl-2-(dicyanomethylidene)-4-oximino-1,3-dithiolane in ether was added at 0° C. to a mixture of 3.02 grams (0.023m) of phosgene and 2.15 grams (0.018m) of N,N-dimethylaniline in ether. After stirring for 2 hours, the salt was filtered and discarded. The filtrate was partially concentrated to remove excess of phosgene. The ethereal chloroformate was cooled to 0° C. and 5.0 grams of 20 percent aqueous dimethylamine was added over a period of 20 minutes. At the end of the reaction the solution was slightly basic. After stirring for an additional period of 15 minutes, it was diluted with 20 ml of water and the solid collected after filtration. Recrystallization from benzene afforded 0.9 grams of solid. m.p. 175°–177° C.

Calc'd for $C_{11}H_{12}N_4O_2S_2$: C, 44.58; H, 4.08; N, 18.92. Found: C, 44.75; H, 4.01; N, 19.00.

EXAMPLE XLIV

Preparation of N,N'-Bis-[[5,5-Dimethyl-2-isopropylimino-4-[O-(N-methylcarbamoyl)oximino]-1,3-dithiolane]]sulfide. (Method V)

To a solution of 4.37 grams (0.02m) of 5,5-dimethyl-2-isopropylimino-4-oximino-1,3-dithiolane and 2.0 grams (0.01m) of bis-(N-methyl-N-fluorocarbonylamino) sulfide in 100 ml of toluene at 25° C. was added 2.02 grams (0.02m) of triethylamine. After stirring for 20 hours the solid was filtered and taken in methylene chloride. The organic solution was washed with water and dried over magnesium sulfate. Concentration under reduced pressure gave a solid residue. Crystallization from ethylacetate afforded 3.8 grams of a solid. m.p. 158°–160° C.

Calc'd for $C_{20}H_{32}N_6O_4S_5$: C, 41.35; H, 5.55; N, 14.47. Found: C, 41.28; H, 5.80; N, 14.39.

The compounds of EXAMPLES XLV — LXXVIII were prepared by the methods of EXAMPLES XL — XLIV. Their physical properties are listed in TABLE III below.

TABLE III
MELTING POINTS AND ELEMENTAL ANALYSIS OF CARBAMOYLOXIME COMPOUNDS $$\underset{R_2}{\overset{R_1}{\phantom{X}}}C\underset{S}{\overset{\phantom{X}}{\diagdown}}\underset{\phantom{X}}{\overset{\phantom{X}}{C}}\underset{\phantom{X}}{\overset{NOZ}{=}}$$

| Example | $R_1$ | $R_2$ | Z | X | MP°C. | Molecular Formula | Calculated C | Calculated H | Calculated N | Found C | Found H | Found N |
|---|---|---|---|---|---|---|---|---|---|---|---|---|
| XLV | $CH_3$ | $CH_3$ | $CH_3$ | $NCH_3$ | 64-68 | $C_9H_{12}Cl_3N_3O_2S_3$ | 27.24 | 3.05 | 10.59 | 27.66 | 3.00 | 10.57 |
| XLVI | $CH_3$ | $CH_3$ | $C(O)N-SCCl_3$ | $NC_2H_5$ | 78-82 | $C_9H_{15}N_3O_2S_2$ | 41.36 | 5.78 | 16.08 | 41.36 | 5.66 | 15.91 |
| XLVII | $CH_3$ | $CH_3$ | $C(O)NHCH_3$ | $N-i-C_3H_7$ | 81-83 | $C_{10}H_{17}N_3O_2S_2$ | 43.61 | 6.22 | 15.25 | 43.80 | 6.05 | 15.18 |
| XLVIII | $CH_3$ | $CH_3$ | $C(O)NHCH_3$ | $N-i-C_3H_7$ | 85-87 | $C_{11}H_{16}Cl_3N_3O_2S_3$ | 31.10 | 3.81 | 9.89 | 31.47 | 5.57 | 9.74 |
| XLIX | $CH_3$ | $CH_3$ | $C(O)N-SCCl_3$ $CH_3$ | $N-i-C_3H_7$ | oil | $C_{14}H_{25}N_3O_2S_4$ | 42.50 | 6.37 | 10.62 | 42.63 | 6.35 | 10.46 |
| L | $CH_3$ | $CH_3$ | $C(O)N-S_2-C(CH_3)_3$ $CH_3$ | $N-t-C_4H_9$ | amorphous solid | $C_{11}H_{19}N_3O_2S_2$ | 45.65 | 6.61 | 14.51 | 45.37 | 6.41 | 14.33 |
| LI | $CH_3$ | $CH_3$ | $C(O)NHCH_3$ | $N-t-C_4H_9$ | 72-74 | $C_{12}H_{18}Cl_3N_3O_2S_3$ | 32.84 | 4.13 | 9.57 | 33.42 | 4.07 | 9.63 |
| LII | $CH_3$ | $CH_3$ | $C(O)N-SCCl_3$ $CH_3$ | $N-C_4H_9$ | 97-99 | $C_{11}H_{19}N_3O_2S_2$ | 45.65 | 6.61 | 14.51 | 45.56 | 6.38 | 14.47 |
| LIII | $CH_3$ | $CH_3$ | $C(O)NHCH_3$ | $N-C_4H_9$ | oil | $C_{12}H_{18}Cl_3N_3O_2S_3$ | 32.84 | 4.13 | 9.57 | 34.02 | 4.25 | 9.29 |
| LIV | $CH_3$ | $CH_3$ | $C(O)N-SCCl_3$ | $N$-cyclo-$C_6H_{11}$ | 155-170 | $C_{13}H_{21}N_3O_2S_2$ | 49.49 | 6.71 | 13.32 | 48.11 | 6.55 | 12.92 |
| LV | $CH_3$ | $CH_3$ | $C(O)NHCH_3$ | $N-N(CH_3)_2$ | 90-94 | $C_9H_{16}N_4O_2S_2$ | 39.11 | 5.84 | 20.27 | 39.08 | 5.63 | 19.82 |
| LVI | $CH_3$ | $CH_3$ | $C(O)NHCH_3$ $CH_3$ | $N-N(CH_3)_2$ | 82-84 | $C_{10}H_{15}Cl_3N_4O_2S_3$ | 28.20 | 3.55 | 13.16 | 29.24 | 3.55 | 12.88 |
| LVII | $CH_3$ | $CH_3$ | $C(O)N-SCCl_3$ | $NSO_2CH_3$ | 104-106 | $C_8H_{13}N_3O_4S_3$ | 30.85 | 4.21 | 13.49 | 31.04 | 4.29 | 13.43 |
| LVIII | $CH_3$ | $CH_3$ | $C(O)NHCH_3$ | $N-SO_2CH_3$ | 141-143 | $C_9H_{12}Cl_3N_3O_4S_4$ | 23.45 | 2.79 | 9.11 | 23.51 | 2.57 | 9.23 |
| LIX | $CH_3$ | $CH_3$ | $C(O)NHCH_3$ | ![benzene ring with CH3 para] $NSO_2$—C$_6$H$_4$—CH$_3$ | 164-165 | $C_{14}H_{17}N_3O_4S_3$ | 43.39 | 4.42 | 10.84 | 43.27 | 4.48 | 10.66 |
| LX | $CH_3$ | $CH_3$ | $C(O)N-SCCl_3$ $CH_3$ | $NSO_2$—C$_6$H$_4$—CH$_3$ | 144-146 | $C_{15}H_{16}Cl_3N_3O_4S_4$ | 33.55 | 3.00 | 7.82 | 33.45 | 2.97 | 7.81 |
| LXI | $CH_3$ | $CH_3$ | $C(O)NHCH_3$ | $C(CN)CO_2C_2H_5$ | 188-196 | $C_{12}H_{15}N_3O_4S_2$ | 43.70 | 4.50 | 12.70 | 43.81 | 4.66 | 12.65 |
| LXII | $CH_3$ | $CH_3$ | $C(O)NHCH_3$ | $C(CN)_2$ | 223-225 | $C_{10}H_{10}N_4O_2S_2$ | 42.54 | 3.57 | 19.84 | 42.49 | 3.51 | 19.74 |

TABLE III-continued
MELTING POINTS AND ELEMENTAL ANALYSIS OF CARBAMOYLOXIME COMPOUNDS $$\begin{array}{c} R_1 \\ | \\ R_2-C \end{array} \begin{array}{c} NOZ \\ \| \\ C \\ / \\ S \end{array} \begin{array}{c} \\ \\ C=X \\ / \\ S \end{array}$$

| Example | X | R₁ | R₂ | Z | MP°C. | Molecular Formula | Calculated C | Calculated H | Calculated N | Found C | Found H | Found N |
|---|---|---|---|---|---|---|---|---|---|---|---|---|
| LXIII | C(CN)₂ | CH₃ | CH₃ | CH₃<br>\|<br>C(O)NSCCl₃ | 149-150 | C₁₁H₉Cl₃N₄O₂S₃ | 30.59 | 2.10 | 12.97 | 30.47 | 1.93 | 13.06 |
| LXIV | C(CN)₂ | CH₃ | CH₃ | CH₃<br>\|<br>C(O)NS₂—C(CH₃)₃ | 103-104 | C₁₄H₁₈N₄O₂S₄ | 41.77 | 4.51 | 13.92 | 41.49 | 4.36 | 13.76 |
| LXV | C(CN)CO₂C₂H₅ | CH₃ | CH₃ | CH₃<br>\|<br>C(O)N—SCCl₃ | 118-119 | C₁₃H₁₄Cl₃N₃O₄S₃ | 32.61 | 2.95 | 8.78 | 32.86 | 3.03 | 8.80 |
| LXVI | C(CN)Ph | CH₃ | CH₃ | C(O)NHCH₃ | 135-136 | C₁₅H₁₅N₃O₂S₂ | 54.05 | 4.50 | 12.60 | 53.74 | 4.32 | 12.55 |
| LXVII | C(NO₂)H | CH₃ | CH₃ | C(O)NHCH₃ | 158-159 | C₈H₁₁N₃O₄S₂ | 34.64 | 3.96 | 15.15 | 34.61 | 3.81 | 15.06 |
| LXVIII | C(COCH₃)H | CH₃ | CH₃ | C(O)NHCH₃ | 143-146 | C₁₀H₁₄N₂O₃S₂ | 43.93 | 4.79 | 10.25 | 43.74 | 5.08 | 10.22 |
| LXIX | NCN | CH₃ | CH₃ | C(O)NHCH₃ | 180-185 | C₈H₁₀N₄O₂S₂ | 37.19 | 3.90 | 21.68 | 37.27 | 3.90 | 21.82 |
| LXX | NCN | CH₃ | CH₃ | CH₃<br>\|<br>C(O)N—SCCl₃ | 128-130 | C₉H₉Cl₃N₄O₂S₃ | 26.51 | 2.22 | 13.74 | 27.06 | 2.45 | 13.67 |
| LXXI | S | CH₃ | CH₃ | C(O)NHCH₃ | 98-99.5 | C₇H₁₀N₂O₂S₃ | 33.58 | 4.02 | 11.19 | 34.30 | 3.80 | 11.16 |
| LXXII | C(CN)₂ | CH₃ | CH₃ | CH₃<br>\|<br>C(O)N—S₂ | 152-154 | C₂₀H₂₂N₄O₂S₄ | 50.18 | 4.63 | 11.71 | 49.98 | 4.58 | 11.62 |
| LXXIII | C(CN)₂ | CH₃ | CH₃ | CH₃<br>\|<br>C(O)N—S— ⌬ —C(CH₃)₃ | 119-122 | C₂₀H₂₂N₄O₂S₃ | 53.78 | 4.97 | 12.55 | 53.60 | 4.81 | 12.41 |
| LXXIV | C(CN)₂ | CH₃ | CH₃ | CH₃<br>\|<br>C(O)N—S—morpholinyl-⌬-C(CH₃)₃ | 141-142 | C₁₄H₁₇N₅O₃S₃ | 42.09 | 4.29 | 17.53 | 42.06 | 4.14 | 17.48 |
| LXXV | C(CN)₂ | CH₃ | CH₃ | CH₃ O CH₃<br>\| \|\| \|<br>C(O)N—S₂—C—CH<br>\| \|<br>CH₃ CH₃ | 96-97 | C₁₇H₂₂N₄O₂S₄ | 44.52 | 4.84 | 12.22 | 44.44 | 4.62 | 12.17 |
| LXXVI | O=CHCCH₃ | H | H | C(O)NHCH₃ | 150-151 | C₈H₁₀N₂O₃S₂ | 39.01 | 4.09 | 11.37 | 38.90 | 4.22 | 11.40 |

TABLE III-continued
MELTING POINTS AND ELEMENTAL ANALYSIS OF CARBAMOYLOXIME COMPOUNDS Structure:

$$\underset{R_2}{\overset{R_1}{\diagup}}C\overset{S}{\underset{S}{\diagdown}}C=NOZ \quad ; \quad C=X$$

(5-membered ring with two S atoms, R₁R₂C, C=NOZ, and C=X substituents)

| Example | X | R₁ | R₂ | Z | MP °C. | Molecular Formula | Calculated C | Calculated H | Calculated N | Found C | Found H | Found N |
|---|---|---|---|---|---|---|---|---|---|---|---|---|
| LXXVII | C(CN)₂ | CH₃ | CH₃ | $-\underset{\underset{O}{\|\|}}{C}-\underset{\underset{CH_3}{\|}}{N}-S-\underset{\underset{CH_3}{\|}}{N}C(O)ON=C\underset{\underset{S-}{\diagdown}}{\overset{\overset{S}{\diagup}}{}}\overset{CH_3}{\underset{}{C-CH_3}}$  ...C=C(CN)₂ | 177–180 | C₂₀H₁₈N₈O₄S₅ | 40.39 | 3.05 | 18.84 | 40.09 | 2.99 | 18.41 |
| LXXVIII | NCH₃ | CH₃ | CH₃ | $-\underset{\underset{O}{\|\|}}{C}-\underset{\underset{CH_3}{\|}}{N}-S-\underset{\underset{CH_3}{\|}}{N}C(O)ON=C\underset{\underset{S-}{\diagdown}}{\overset{\overset{S}{\diagup}}{}}\overset{CH_3}{\underset{}{C-CH_3}}$  ...C=NCH₃ | 124–125 | C₁₆H₂₄N₆O₄S₅ | 36.62 | 4.61 | 16.02 | 36.52 | 4.54 | 15.71 |

The following compounds are representative of other compounds that are within the scope of this invention which can be prepared according to this invention by selecting appropriate starting materials for use in the procedures described above:

5,5-Dimethyl-2-methylimino-4-[[O-[N-methyl-N-(4-tert-butylphenylsulfenyl)carbamoyl]oximino]]1,3-dithiolane.

2-Isopropylimino-4-[[O-[N-butyl-N-(4-nitrophenylsulfenyl)carbamoyl]oximino]]-1,3-dithiolane.

5,5-Dimethyl-2-octylimino-4-[[O-[N-methyl-N-(cyclohexylthiosulfenyl)carbamoyl]oximino]]-1,3-dithiolane.

5-Butyl-2-isopropylimino-4-[[O-[N-methyl-N-(2,4-dimethyl-3-oxo-2-pentanesulfenyl)carbamoyl]oximino]]-1,3-dithiolane.

5,5-Dimethyl-2-ethylimino-4-[[O-[N-methyl-N-(2-chloro-2-propanethiosulfenyl)carbamoyl]oximino]]-1,3-dithiolane.

5,5-Dimethyl-2-methylimino-4-[[O-[N-methyl-N-(trichloromethanesulfenyl)carbamoyl]oximino]]-1,3-dithiolane.

5,5-Dimethyl-2-(dicyanomethylidene)-4-[[O-[N-methyl-N-(diethylaminosulfenyl)carbamoyl]oximino]]-1,3-dithiolane.

5,5-Dimethyl-2-(dicyanomethylidene)-4-[[O-[N-methyl-N-(morpholinosulfenyl)carbamoyl]oximino]]-1,3-dithiolane.

5,5-Dimethyl-2-(dimethylhydrazono)-4-[[O-[N-methyl-N-(1,1,2,2-tetrachloroethanesulfenyl)carbamoyl]oximino]]-1,3-dithiolane.

5,5-Dimethyl-2-(nitromethylidene)-4-[[O-[N-methyl-N-acetylcarbamoyl]oximino]]-1,3-dithiolane.

5,5-Dimethyl-2-(2-oxopropylidene)-4-[[O-[N-methyl-N-chloroacetylcarbamoyl]oximino]]-1,3-dithiolane.

5,5-Dimethyl-2-methylimino-4-[[O-[N-methyl-N-(butylsulfenyl) carbamoyl]oximino]]-1,3-dithiolane.

5,5-Dimethyl-2-isopropylimino-4-[[O-[N-methyl-N-(4-t-butylphenylthiosulfenyl)carbamoyl]oximino]]-1,3-dithiolane.

5,5-Dimethyl-2-(cyanoethoxycarbonylmethylidene)-4-[[O-[N-methyl-N-(2-benzoyl-2-propanethiosulfenyl) carbamoyl]oximino]]-1,3-dithiolane.

5,5-Dimethyl-2-methylimino-4-[[O-N-methyl-N-(3,4-dichlorophenylthiosulfenyl)carbamoyl]oximino]]-1,3-dithiolane.

5,5-Dimethyl-2-isopropylimino-4-[[O-N-methyl-N-(3-trifluoromethylphenylthiosulfenyl)carbamoyl]oximino]]-1,3-dithiolane.

5,5-Dimethyl-2-methylimino-4-[[O-N-methyl-N-(4-cyano-2-methoxyphenylsulfenyl)carbamoyl]oximino]]-1,3-dithiolane.

5,5-Dimethyl-2-(dimethylhydrazono)-4-[[O-N-methyl-N-(2-methyl-2-propanethiosulfenyl)carbamoyl]oximino]]-1,3-dithiolane.

5,5-Dimethyl-2-methylimino-4-[[O-N-methyl-N-(4-phenylphenylsulfenyl)carbamoyl]oximino]]-1,3-dithiolane.

5,5-Dimethyl-2-methylimino-4-[[O-N-methyl-N-(3-phenoxyphenylsulfenyl)carbamoyl]oximino]]-1,3-dithiolane.

5,5-Dibutyl-2-methylimino- 4-oximino-1,3-dithiolane.

5,5-Dimethyl-2-(2-methyl-4-chlorophenylimino)-4-oximino-1,3-dithiolane.

5,5-Dimethyl-2-(4-chlorophenylhydrazono)-4-oximino-1,3-dithiolane.

5,5-Dimethyl-2-nitroethylidene-4-oximino-1,3-dithiolane.

5,5-Dimethyl-2-diethoxycarbonylmethylidene-4-oximino-1,3-dithiolane.

5,5-Dimethyl-2-(4-cyanophenylhydrazono)-4-oximino-1,3-dithiolane.

5,5-Dimethyl-2-(4-trifluoromethylphenylimino)-4-oximino-1,3-dithiolane.

5,5-Dimethyl-2-(4-nitrophenylhydrazono)-4-oximino-1,3-dithiolane.

N,N'-Bis-[[5,5-Dimethyl-2-N,N-dimethylhydrazono-4-[O-N-methylcarbamoyl)oximino]-1,3-dithiolane]]sulfide.

N,N'-Bis[[5,5-Dimethyl-2-nitromethylidene-4[O-(N-methylcarbamoy)oximino]-1,3-dithiolane]]sulfide.

Selected species of the new compounds were evaluated to determine their pesticidal activity against mites and certain insects, including anaphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae Scop.*) reared on potted dwarf nasturtium plants at 65°–70° F. and 50–70 per cent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 per cent, respectively. Aphids which fell into the paper and were unable to remain standing after being uprighted were considered dead. Aphids remaining on the plants wre observed closely for movement and those which were unable to move the length of the body upon stimulator by prodding were considered dead. Per cent mortality was recorded for various concentration levels.

Southern Armyworm Leaf Spray Test

Larvae of the southern armyworm (*Prodenia Eridania*, (Cram.), reared on Tendergreen bean plants at a temperature of 80°±5° F. and a relative humidity of 50±5 per cent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–100 milliliters of test compound formulation by use of a DeVilbiss spray gun set at 10 psig. air pressure.

This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petric dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Per cent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 per cent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°–5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialities Manufacturing Association (Blue Book, McNair-Dorland Co., NY., 1954; pages 234–244, 261) under controlled conditions of 80°±5° F. and 50±5 per cent relative humidity, were the test insects. The flies were immobilized by anesthetizing with carbon dioxide and twenty five immobilized individuals, males and females, were transferred to a cage consisting of a standard food stainer about five inches in diameter which was inverted over a wrapping-paper-covered surface. The test compounds were formulated by diluting the stock suspension with a 10 per cent (by weight) sugar solution to give a suspension containing 500 parts of test compound per million parts of final formulation, by weight. Ten milliliters of the test formulation were added to a souffle cup containing a one inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 per cent. Flies which showed no sign of movement on prodding were considered dead.

Mite Foilage Spray Test

Adults and nymphal stages of the two spotted mite (*Tetranychus urticae Koch*), reared on Tendergreen bean plants at 80±5 per cent relative humidity, were the test organisms. Infested leaves from a stock culture were placed on the primary leaves of two bean plants six to eight inches in height, growing in a two-and-a-half inch clay pot. 150–200 mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted for 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 per cent relative humidity for six days, after which a mortality count of motile forms were made. Microscopic examination for motile forms was made on the leaves of the test plants. Any individual which was capable of locomotion upon prodding, was considered living.

The results of these tests are set forth in Table I below. In these tests the pesticidal activity of the compounds against aphid, mite, Southern Armyworm, Mexican Bean Beetle, and house fly was rated as follows:

A = Excellent control
B = Partial control
C = No control

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these test are set forth in Table VI below:

TABLE IV

BIOLOGICAL ACTIVITY

| Example | Structure | Bean Aphid | Mite | Southern Armyworm | Mexican Bean Beetle | House-Fly | A. O. Rat (mg/kg) |
|---------|-----------|------------|------|-------------------|---------------------|-----------|-------------------|
| XL | 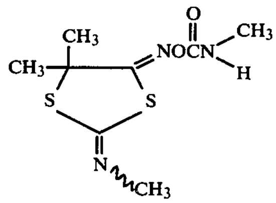 | A | A | B | A | A | — |
| XLV | 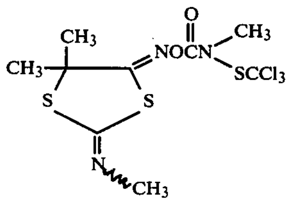 | A | A | A | A | A | — |
| XLVI | 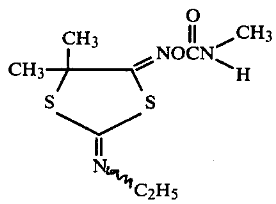 | A | C | B | A | A | 6.3 |
| XLI | 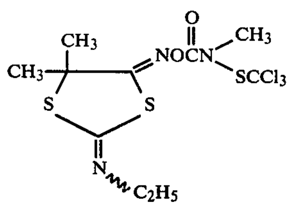 | A | A | B | A | A | — |
| XLVII | 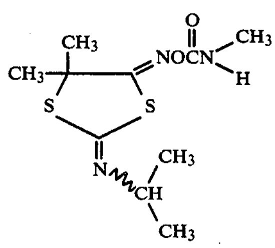 | A | A | C | A | A | 8.9 |
| XLVIII | 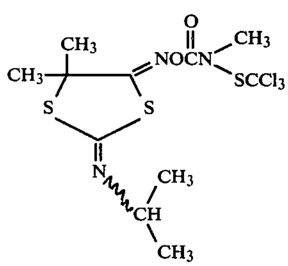 | A | A | C | A | A | 226 |
| XLIX | 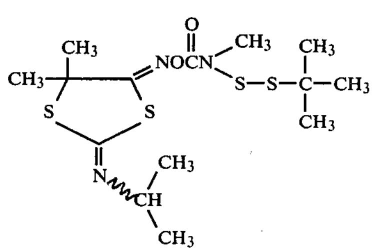 | A | A | C | A | A | — |

TABLE IV-continued

BIOLOGICAL ACTIVITY

| Example | Structure | Bean Aphid | Mite | Southern Armyworm | Mexican Bean Beetle | House-Fly | A. O. Rat (mg/kg) |
|---|---|---|---|---|---|---|---|
| L | (structure) | A | A | B | A | A | 31.5 |
| LI | (structure) | A | B | C | A | A | — |
| LII | (structure) | A | C | B | A | A | — |
| LIII | (structure) | A | A | C | A | A | — |
| LIV | (structure) | A | B | C | B | A | — |
| LV | (structure) | A | A | A | A | A | 1.8 |
| LVI | (structure) | A | A | A | A | A | 3.5 |

TABLE IV-continued
BIOLOGICAL ACTIVITY

| Example | Structure | Bean Aphid | Mite | Southern Armyworm | Mexican Bean Beetle | House-Fly | A. O. Rat (mg/kg) |
|---------|-----------|------------|------|-------------------|---------------------|-----------|-------------------|
| XLII | [structure] | A | A | A | A | A | — |
| LVII | [structure] | B | C | B | B | B | — |
| LVIII | [structure] | C | C | C | B | B | — |
| LIX | [structure] | C | C | C | C | C | — |
| LX | [structure] | C | C | B | B | B | — |
| LXI | [structure] | C | C | C | A | C | — |
| LXII | [structure] | C | C | C | C | C | — |
| XLIII | [structure] | B | C | C | B | B | — |

TABLE IV-continued
BIOLOGICAL ACTIVITY

| Example | Structure | Bean Aphid | Mite | Southern Armyworm | Mexican Bean Beetle | House-Fly | A. O. Rat (mg/kg) |
|---|---|---|---|---|---|---|---|
| LXIII | [structure] | A | C | C | A | C | 538.0 |
| LXIV | [structure] | A | C | B | A | B | — |
| LXV | [structure] | B | C | C | A | A | — |
| LXVI | [structure] | C | C | C | B | C | — |
| LXVII | [structure] | B | C | A | A | A | — |
| LXVIII | [structure] | A | C | A | A | A | — |
| LXIX | [structure] | C | C | C | C | C | — |
| LXX | [structure] | C | C | C | C | C | — |

TABLE IV-continued
BIOLOGICAL ACTIVITY

| Example | Structure | Bean Aphid | Mite | Southern Armyworm | Mexican Bean Beetle | House-Fly | A. O. Rat (mg/kg) |
|---|---|---|---|---|---|---|---|
| LXXI | 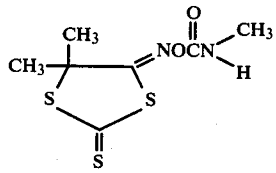 | A | B | B | A | B | — |
| LXXII | 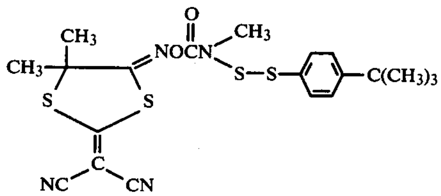 | A | C | C | A | C | — |
| LXXIII | 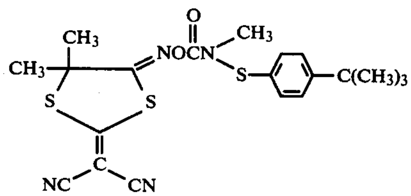 | A | B | C | A | C | — |
| LXXIV | 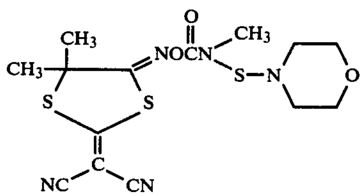 | A | C | B | C | C | — |
| LXXV | 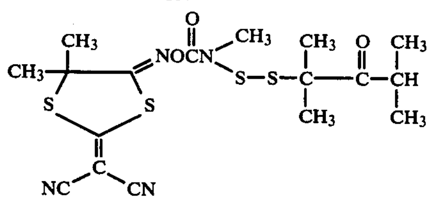 | A | A | B | B | C | — |
| LXXVI | 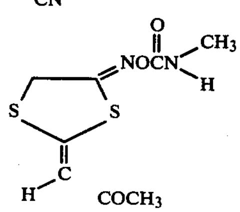 | C | C | C | B | A | — |
| XLIV | 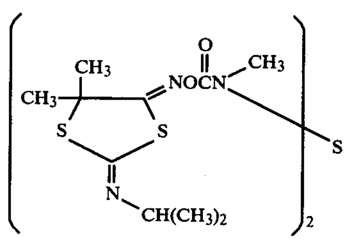 | B | C | C | A | B | 113.0 |
| LXXVII | 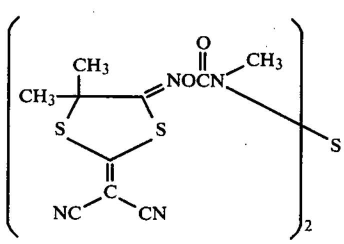 | C | C | C | A | C | — |

TABLE IV-continued

BIOLOGICAL ACTIVITY

| Example | Structure | Bean Aphid | Mite | Southern Armyworm | Mexican Bean Beetle | House-Fly | A. O. Rat (mg/kg) |
|---|---|---|---|---|---|---|---|
| LXXVIII | 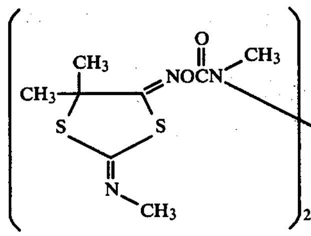 | A | A | A | A | A | — |

The date in TABLE VI clearly illustrates the broad spectrum high level pesticidal activity exhibited by the compounds of this invention. It should be understood that the pests evaluated are representative of a wider variety of pest which can be controlled by the compounds of this invention.

The compound contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 per cent by weight and in the solid formulations from about 0.5 to about 90 per cent by weight. Satisfactory sprays, dusts, or granules for general use contain from about ¼ to 15 pounds of active toxicant per acre.

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. Mixtures of the active compounds of this invention may be used as well as combinations of the active compounds with other biologically active compounds.

What is claimed is:

1. A compound of the formula:

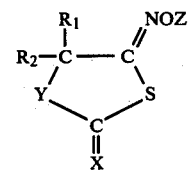

wherein:

Z is

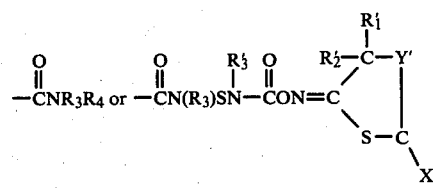

or hydrogen;

$R'_1$, $R'_2$, $R_1$ and $R_2$ are individually hydrogen or alkyl; $R_3$ and $R_4$ are individually hydrogen or alkyl; or when $R_3$ is alkyl, $R_4$ may also be alkanoyl, haloalkanoyl, trihalomethanesulfenyl, tetrahaloethanesulfenyl, dialkylaminosulfenyl, morpholinosulfenyl or either unsubstituted or substituted cycloalkylsulfenyl, cycloalkylthiosulfenyl, alkylsulfenyl, phenylsulfenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination;
$R_3'$ is alkyl;
Y' and Y are individually sulfur, sulfinyl or sulfonyl;
X' and X are individually sulfur,

or $=N-R_7$ wherein:
$R_5$ and $R_6$ are individually hydrogen, alkyl, alkanoyl, alkoxycarbonyl, nitro, cyano or either substituted or unsubstituted phenyl where in the permissible substituents are from 1 to 3 fluoro, chloro, cyano, nitro or trihalomethyl substituents in any combination with the proviso that both $R_5$ and $R_6$ may not be hydrogen, alkyl or phenyl;
$R_7$ is alkyl, cycloalkyl, cyano, dialkylamino, alkylsulfonyl or either substituted or unsubstituted phenyl, phenylamino or phenylsulfonyl wherein the permissible substituents are from 1 to 3 fluoro, chloro, cyano, nitro or trihalomethyl substituents in any combination; with the proviso that $R'_1$, $R'_2$, $R_1$, $R_2$, $R_3$, $R_4$, $R'_3$, $R_5$, $R_6$ and $R_7$ substituents individually may not include more than eight aliphatic carbon atoms.

2. A compound according to claim 1 wherein Z is hydrogen.

3. A compound according to claim 1 wherein Z is

4. A compound according to claim 1 wherein Z is

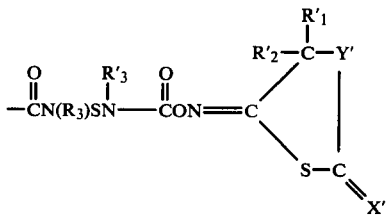

5. A compound according to claim 1 wherein $R'_1$, $R'_2$, $R_1$ and $R_2$ are individually hydrogen or alkyl having from 1 to 4 carbon atoms.

6. A compound according to claim 1 wherein $R'_1$, $R'_2$, $R_1$ and $R_2$ are individually hydrogen or methyl.

7. A compound according to claim 1 wherein $R_3$ and $R_4$ are individually hydrogen or alkyl having from 1 to 4 carbon atoms.

8. A compound according to claim 1 wherein $R_3$ and $R_4$ are individually hydrogen or methyl.

9. A compound according to claim 1 wherein $R_4$ is trihalomethanesulfenyl, dialkylaminosulfenyl, morpholinosulfenyl or either substituted or unsubstituted alkylsulfenyl, phenylsulfenyl, phenylthiosulfenyl or alkylthiosulfenyl wherein the permissible substituents are one or more fluoro, chloro, bromo, trifluoromethyl, alkyl, alkanoyl or aroyl substituents.

10. A compound according to claim 1 wherein $R'_3$ is alkyl having from 1 to 4 carbon atoms.

11. A compound according to claim 1 wherein $R_4$ is trichloromethanesulfenyl, morpholinosulfenyl, alkylphenylsulfenyl, alkylphenylthiosulfenyl, alkylsulfenyl, alkylthiosulfenyl or alkanoylalkylthiosulfenyl.

12. A compound according to claim 1 wherein Y' and Y is sulfur.

13. A compound according to claim 1 wherein Y' and Y are sulfinyl.

14. A compound according to claim 1 wherein Y' and Y are sulfonyl.

15. A compound according to claim 1 wherein X' and X are individually

and where $R_5$ and $R_6$ are individually nitro, cyano, alkoxycarbonyl, phenyl or alkanoyl.

16. A compound according to claim 1 wherein X' and X are sulfur.

17. A compound according to claim 1 wherein X' and X are individually $-N-R_7$ and where $R_7$ is cyano, alkyl, cycloalkyl, dialkylmino, alkylsulfonyl or alkylphenylsulfonyl.

18. 5,5-Dimethyl-2-methylimino-4-oximino-1,3-dithiolane.

19. 5,5-Dimethyl-2-isopropylimino-4-oximino-1,3-dithiolane.

20. 5,5-Dimethyl-2-dicyanomethylidene-4-oximino-1,3-dithiolane.

21. 5,5-Dimethyl-2-nitromethylidene-4-oximino-1,3-dithiolane.

22. 5,5-Dimethyl-2-methylimino-4-[O-(N-methylcarbamoyl)oximino]-1,3-dithiolane.

23. 5,5-Dimethyl-2-tert-butylimino-4-[O-(N-methylcarbamoyl)oximino]-1,3-dithiolane.

24. 5,5-Dimethyl-2-isopropylimino-4-[[O-[(N-methyl-N-trichloromethanesulfenyl)carbamoyl]oimino]]-1,3-dithiolane.

25. 5,5-Dimethyl-2-methylimino-4-[[O-[(N-methyl-N-trichloromethanesulfenyl)carbamoyl]oimino]]-1,3-dithiolane.

26. 5,5-Dimethyl-2-(N',N'-dimethylhydrazono)-4-[O-[[N-methyl-N-(tert-butylthiosulfenyl)]carbamoyl]oximino]-1,3-dithiolane.

27. 5,5-Dimethyl-2-(dicyanomethylidene)-4-[[O-[N-methyl-N-(tert-butylthiosulfenyl)carbamoyl]-oximino]]-1,3-dithiolane.

28. 5,5-Dimethyl-2-(dicyanomethylidene)-4-[[O-[(N-methyl-N-trichloromethylsulfenyl)carbamoyl]oximino]]-1,3-dithiolane.

29. 5,5-Dimethyl-2-(dicyanomethylidene)-4-[[O-[N-methyl-N-(4-tert-butylphenylthiosulfenyl)carbamoyl]oximino]]-1,3-dithiolane.

30. 5,5-Dimethyl-2-(dicyanomethylidene)-4-[[O-[N-methyl-N-(2,4-dimethyl-3-oxo-2-pentanethiosulfenyl)carbamoyl]oximino]]-1,3-dithiolane.

31. N,N'-bis-[[5,5-Dimethyl-2-isopropylimino-4-[O-(N-methylcarbamoyl)oximino]-1,3-dithiolane]]sulfide.

32. N,N'-bis-[[5,5-Dimethyl-2-methylimino-4-[O-(N-methylcarbamoyl)oximino]-1,3-dithiolane]]sulfide.

33. An insecticidal and miticidal composition comprising an acceptable carrier and as the active toxicant an insecticidally or miticidally effective amount of a compound of the formula:

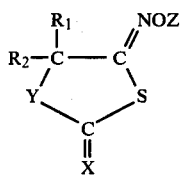

wherein: Z is

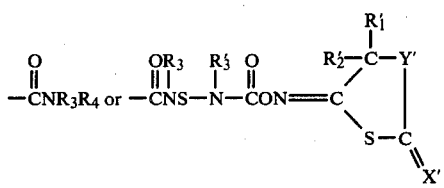

$R_1'$, $R_2'$, $R_1$ and $R_2$ are individually hydrogen or alkyl; $R_3$ and $R_4$ are individually hydrogen or alkyl or when $R_3$ is alkyl, $R_4$ may also be alkanoyl, haloalkanoyl, trihalomethanesulfenyl, tetrahaloethane sulfenyl, dialkylaminosulfenyl, morpholinosulfenyl or either unsubstituted or substituted cycloalkylsulfenyl, cycloalkylthiosulfenyl, alkylsulfenyl, phenylsufenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination;

$R_3'$ is alkyl;

$Y'$ and $Y$ are individually sulfur, sulfinyl or sulfonyl;

$X'$ and $X$ are individually sulfur,

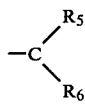

or $-N-R_7$ wherein:

$R_5$ and $R_6$ are individually hydrogen, alkyl, alkanoyl, alkoxycarbonyl, nitro, cyano or either substituted or unsubstituted phenyl wherein the permissible substituents are from 1 to 3 fluoro, chloro, cyano, nitro or trihalomethyl sibstituents in any combination with the proviso that both $R_5$ and $R_6$ may not be hydrogen, alkyl or phenyl;

$R_7$ is alkyl, cycloalkyl, cyano, dialkylamino, alkysulfonyl or either substituted or unsubstituted phenyl, phenylamino or phenylsulfonyl wherein the permissible substitents are from 1 to 3 fluoro, chloro, cyano, nitro or trihalomethyl substituents in any combination; with the proviso that $R_1'$, $R_2'$, $R_1$, $R_2$, $R_3$, $R_4$, $R_3'$, $R_5$, $R_6$ and $R_7$ substituents individually may not include more than eight aliphatic carbon atoms.

34. A composition according to claim 33 wherein z is

35. A composition according to claim 33 wherein Z is

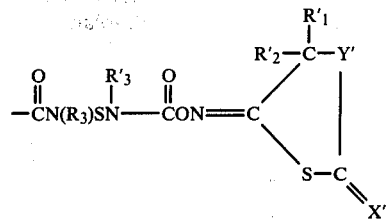

36. A composition according to claim 33 wherein $R_1'$, $R_2'$, $R_1$ and $R_2$ are individually hydrogen or alkyl having from 1 to 4 carbon atoms.

37. A composition according to claim 33 wherein $R_1'$, $R_2'$, $R_1$ and $R_2$ are individually hydrogen or methyl.

38. A composition according to claim 33 wherein $R_3$ and $R_4$ are individually hydrogen or alkyl having from 1 to 4 carbon atoms.

39. A composition according to claim 33 $R_3$ and $R_4$ are individually hydrogen or methyl.

40. A composition according to claim 33 wherein $R_4$ is trihalomethanesulfenyl, dialkylaminosulfenyl, morpholinosulfenyl or either substituted or unsubstituted alkylsulfenyl, phenylsulfenyl, phenylthiosulfenyl or alkylthiosulfenyl wherein the permissible substituents are one or more fluoro, chloro, bromo, trifluoromethyl, alkyl or alkanoyl substituents.

41. A composition according to claim 33 wherein $R_3'$ is alkyl having from 1 to 4 carbon atoms.

42. A composition according to claim 33 wherein $R_4$ is trichloromethanesulfenyl, morpholinosulfenyl, alkylphenylsulfenyl, alkylphenylthiosulfenyl, alkylsulfenyl, alkythiosulfenyl or alkanoylalklthiosulfenyl.

43. A composition according to claim 33 wherein $Y'$ and $Y$ is sulfur.

44. A composition according to claim 33 wherein $Y'$ and $Y$ are sulfinyl.

45. A composition according to claim 33 wherein $Y'$ and $Y$ are sulfonyl.

46. A composition according to claim 33 wherein $X'$ and $X$ are individually

and where $R_5$ and $R_6$ are individually nitro, cyano, alkoxycarbonyl, phenyl or alkanoyl.

47. A composition according to claim 33 wherein $X'$ and $X$ are sulfur.

48. A composition according to claim 33 wherein $X'$ and $X$ are individually $-N-R_7$ wherein $R_7$ is cyano, alkyl, cycloalkyl, dialkylamino, alkylsulfonyl or alkylphenylsulfonyl.

49. A composition according to claim 33 wherein the active toxicant is 5,5-Dimethyl-2-methylimino-4-[O-(N-methylcarbamoyl)oximino]-1,3-dithiolane.

50. A composition according to claim 33 wherein the active toxicant is 5,5-Dimethyl-2-tert-butylimino-4-[O-(N-methylcarbamoyl)oximino]-1,3-dithiolane.

51. A composition according to claim 33 wherein the active toxicant is 5,5-Dimethyl-2-isopropylimino-4[[O-(N-methyl-N-trichloromethanesulfenyl)carbamoyl]oximino]]-1,3-dithiolane.

52. A composition according to claim 33 wherein the active toxicant is 5,5-Dimethyl-2-(N', N'-dimethylhydrazono-4-[[O-[N-methyl-N-trichloro-methanesulfenyl)carbamoyl]oximino]]-1,3-dithiolane.

53. A composition according to claim 33 wherein the active toxicant is 5,5-Dimethyl-2-[N', N'-dimethylhydrazono-4-[[O-[N-methyl-N-tert-butylthiosulfenyl)]carbamoyl]oximino]]-1,3-dithiolane.

54. A composition according to claim 33 wherein the active toxicant is 5,5-Dimethyl-2-(dicyanomethylidene)-4-[[O-[N-methyl-N-(tert-butylthiosulfenyl)-carbamoyl]oximino]]-1,3-dithiolane.

55. A composition according to claim 33 wherein the active toxicant is 5,5-dimethyl-2-(dicyanomethylidene)-4-[[O-[(N-methyl-N-trihloromethylsulfenyl)carbamoyl]oximino]]-1,3-dithiolane.

56. A composition according to claim 33 wherein the active toxicant is 5,5-dimethyl-2-(dicyanomethylidene)-4-[[O-[N-methyl-N-(4-tert-butylphenylthiosulfenyl)carbamoyl]oximino]]-1,3-dithiolane.

57. A composition according to claim 33 wherein the active toxicant is 5,5-dimethyl-2-(dicyanomethylidene)-4-[[O-[N-methyl-N-(2,4-dimethyl-3-oxo-2-pentanethiosulfenyl)carbamoyl]oximino]]-1,3-dithiolane.

58. A composition according to claim 33 wherein the active toxicant is N,N'-bis-[5,5-dimethyl-2-isopropylimino-4-[O-(N-methylcarbamoyl)oximino]-1,3-dithiolane]sulfide.

59. A composition according to claim 33 wherein the active intoxicant is N,N'-bis-[5,5-dimethyl-2-methylimino-4-[O-(N-methylcarbamoyl)oximino]-1,3-dithiolane]]sulfide.

60. A method of controlling insects and mites which comprises subjecting them to an insecticidally or miticidally effective amount of a compound of the formula:

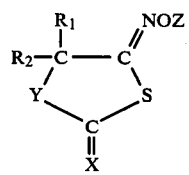

wherein:
Z is

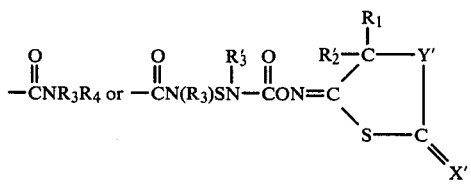

$R'_1$, $R'_2$, $R_1$ and $R_2$ are individually hydrogen or alkyl;
$R_3$ and $R_4$ are individually hydrogen or alkyl; or when $R_3$ is alkyl, $R_4$ may also be alkanoyl, haloalkanoyl, trihalomethanesulfenyl, tetrahaloethanesulfenyl, dialkylaminosulfenyl, morpholinosulfenyl or either unsubstituted or substituted cycloalkylsulfenyl, cycloalkylthiosulfenyl, alkylsulfenyl, phenylsulfenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination,
$R'_3$ is alkyl;
Y' and Y are individually sulfur, sulfinyl or sulfonyl;
X' and X are individually sulfur,

or —N—$R_7$;
wherein:
$R_5$ and $R_6$ are individually hydrogen, alkyl, alkanoyl, alkoxycarbonyl, nitro, cyano or either substituted or unsubstituted phenyl wherein the permissible substituents are from 1 to 3 fluoro, chloro, cyano, nitro or trihalomethyl substituents in any combination with the proviso that both $R_5$ and $R_6$ may not be hydrogen, alkyl or phenyl;
$R_7$ is alkyl, cycloalkyl, cyano, dialkylamino alkylsulfonyl or either substituted or unsubstituted phenyl, phenylamino or phenylsulfonyl wherein the permissible substituents are from 1 to 3 fluoro, chloro, cyano, nitro or trihalomethyl substituents in any combination; with the proviso that $R'_1$, $R'_2$, $R_1$, $R_2$, $R_3$, $R_4$, $R'_3$, $R_5$ $R_6$ and $R_7$ substituents individually may not include more than eight aliphatic carbon atoms.

61. A method according to claim 60 wherein Z is

62. A method according to claim 60 wherein Z is

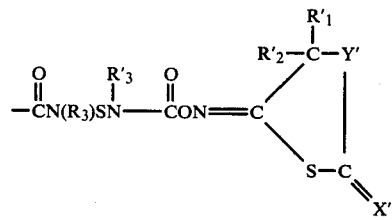

63. A method according to claim 60 wherein $R'_1$, $R'_2$, $R_1$ and $R_2$ are individually hydrogen or alkyl having from 1 to 4 carbon atoms.

64. A method according to claim 60 wherein $R'_1$, $R'_2$, $R_1$ and $R_2$ are individually hydrogen or methyl.

65. A method according to claim 60 wherein $R_3$ and $R_4$ are individually hydrogen or alkyl having from 1 to 4 carbon atoms.

66. A method according to claim 60 wherein $R_3$ and $R_4$ are individually hydrogen or methyl.

67. A method according to claim 60 wherein $R_4$ is trihalomethanesulfenyl, dialkylaminosulfenyl, morpholinosulfenyl or either substituted or unsubstituted alkylsulfenyl, phenylsulfenyl, phenylthiosulfenyl or alkylthiosulfenyl wherein the permissible subsituents are one or more fluoro, chloro, bromo, trifluoromethyl, alkyl or alkanoyl substituents.

68. A method according to claim 60 wherein $R'_3$ is alkyl.

69. A method according to claim 60 wherein $R_4$ is trichloromethanesulfenyl, morpholinosulfenyl, alkylphenylsulfenyl, alklphenylthiosulfenyl, alkysulfenyl, alkylthiosulfenyl or alkanoylalkylthiosulfenyl.

70. A method according to claim 60 wherein Y' and Y is sulfur.

71. A method according to claim 60 wherein Y' and Y are sulfinyl.

72. A method according to claim 60 wherein Y' and Y are sulfonyl.

73. A method according to claim 60 wherein X' and X are individually

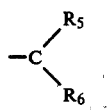

and where $R_5$ and $R_6$ are individually nitro, cyano, alkoxycarbonyl, phenyl or alkanoyl.

74. A method according to claim 60 wherein X' and X are sulfur.

75. A method according to claim 60 wherein X' and X are individually —N—$R_7$ and where $R_7$ is cyano, alkyl, cycloalkyl, dialkylamino, alkylsulfonyl, or alkylphenylsulfonyl.

76. A method according to claim 60 wherein the compound is 5,5-dimethyl-2-methylimino-4-[O-(N-methylcarbamoyl)oximino]-1,3-dithiolane.

77. A method according to claim 60 wherein the compound is 5,5-dimethyl-2-tert-butylimino-4-]O-(N-methylcarbamoyl)oximino]-1,3-dithiolane.

78. A method according to claim 60 wherein the compound is 5,5-dimethyl-2-isopropylimino-4-[[O-[(N-methyl-N-trichloromethanesulfenyl)carbamoyl]oximino]]-1,3-dithiolane.

79. A method according to claim 60 wherein the compound is 5,5-dimethyl-2-methylimino-4-[[O-[(N-methyl-N-trichloromethanesulfenyl)carbamoyl]oximino[]-1,3-dithiolane.

80. A method according to claim 60 wherein the compound is 5,5-dimethyl-2-(N'-N'-dimethylhydrazono-4-[[O-[N-methyl-N-(tert-butylthiosulfenyl)-]carbamoyl]oximino]]-1,3-dithiolane.

81. A method according to claim 60 wherein the compound is 5,5-dimethyl-2-(dicyanomethylidene)-4-[[O-[N-methyl-N-(tert-butylthiosulfenyl)carbamoyl]oximino]]-1,3-dithiolane.

82. A method according to claim 60 wherein the compound is 5,5-dimethyl-2-(dicyanomethylidene)-4-[[O-[N-methyl-N-trichloromethylsulfenyl)carbamoyl]oximino]]-1,3-dithiolane.

83. A method according to claim 60 wherein the compound is 5,5-dimethyl-2-(dicyanomethylidene)-4-[[O-[N-methyl-N-(4-tert-butylphenylthiosulfenyl)carbamoy]oximino]]-1,3-dithiolane.

84. A method according to claim 60 wherein the compound is 5,5-dimethyl-2-(dicyanomethylidene)-4-[[O-[N-methyl-N-(2,4-dimethyl-3-oxo-2-pentanethiosulfenyl)carbamoyl]oximino]]-1,3-dithiolane.

85. A method according to claim 60 wherein the compound is N,N'-bis-[[5,5-dimethyl-2-isopropylimino-4-[O-(N-methylcarbamoy)oximino]-1,3-dithiolane]]sulfide.

86. A method according to claim 60 wherein the compounds is N,N'-bis-[[5,5-dimethyl-2-methylimino-4-[O-(N-methylcarbamoyl)oximino]-1,3-dithiolane]]sulfide.

87. A method of preparing a compound of the formula:

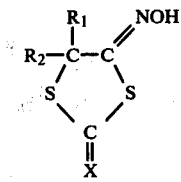

which comprises reacting a compound of the formula:

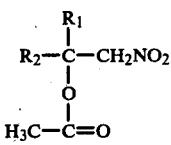

with a compound of the formula:

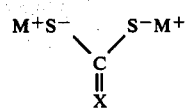

wherein:

$M^+$ is an alkali metal cation;

$R_1$ and $R_2$ are individually hydrogen or alkyl;

X is sulfur;

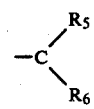

or —N—$R_7$, wherein;

$R_5$ and $R_6$ are individually hydrogen, alkyl, alkanoyl, alkoxycarbonyl, nitro, cyano or either substituted or unsubstituted phenyl wherein the permissible substituents are from 1 to 3 fluoro, chloro, cyano, nitro or trihalomethyl substituents in any combination with the proviso that both $R_5$ and $R_6$ may not be hydrogen, alkyl or phenyl;

$R_7$ is alkyl, cycloalkyl, cyano, dialkylamino, alkylsulfonyl or either substituted or unsubstituted phenyl, phenylamino or phenylsulfonyl wherein the permissible substituents are from 1 to 3 fluoro, chloro, cyano, nitro or trihalomethyl substituents in any combination; with the proviso that $R_1$, $R_2$, $R_5$, $R_6$ and $R_7$ substituents individually may not include more than eight aliphatic carbon atoms.

88. A compound of the formula:

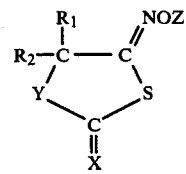

wherein:

Z is

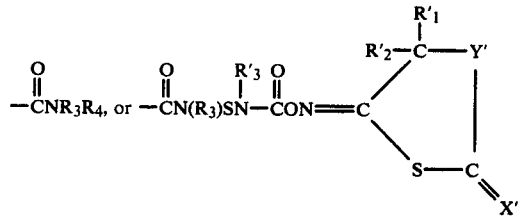 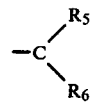

$R'_1$, $R'_2$, $R_1$ and $R_2$ are individually hydrogen or alkyl;

$R_3$ and $R_4$ are individually hydrogen or alkyl; or when $R_3$ is alkyl, $R_4$ may also be alkanoyl, haloalkanoyl, trihalomethanesulfenyl, tetrahaloethanesulfenyl, dialkylaminosulfenyl, morpholinosulfenyl or either unsubstituted or substituted cycloalkylsulfenyl, cycloalkylthiosulfenyl, alkylsulfenyl, phenylsulfenyl, alkylthiosulfenyl or phenylthiosulfenyl wherein the permissible substituents are one or more fluoro, chloro, bromo, aroyl, cyano, nitro, alkyl, alkanoyl, alkoxy, phenyl, phenoxy or trihalomethyl substituents in any combination;

$R'_3$ is alkyl;

$Y'$ and $Y$ are individually sulfur, sulfinyl or sulfonyl;

$X'$ and $X$ are individually sulfur or —N—$R_7$ wherein:

$R_5$ and $R_6$ are individually hydrogen, alkyl, alkanoyl, alkoxycarbonyl, nitro, cyano or either substituted or unsubstituted phenyl where in the permissible substituents are from 1 to 3 fluoro, chloro, cyano, nitro or trihalomethyl substituents in any combination with the proviso that both $R_5$ and $R_6$ may not be hydrogen, alkyl or phenyl;

$R_7$ is alkyl, cycloalkyl, cyano, dialkylamino alkylsulfonyl or either substituted or unsubstituted phenyl, phenylamino or phenylsulfonyl wherein the permissible substituents are from 1 to 3 fluoro, chloro, cyano, nitro or trihalomethyl substituents in any combination; with the proviso that $R'_1$, $R'_2$, $R_1$, $R_2$, $R_3$, $R_4$, $R'_3$ $R_5$, $R_6$ and $R_7$ substituents individually may not include more than eight aliphatic carbon atoms.

* * * * *

UNITED STATES PATENT AND TRADEMARK OFFICE
CERTIFICATE OF CORRECTION

PATENT NO. : 4,156,731
DATED : May 29, 1979
INVENTOR(S) : T.D.J. D'Silva

It is certified that error appears in the above-identified patent and that said Letters Patent are hereby corrected as shown below:

Column 4, line 55, "-20°C" should read -- -10°C --.

Signed and Sealed this

Twenty-fifth Day of September 1979

[SEAL]

Attest:

LUTRELLE F. PARKER

Attesting Officer     Acting Commissioner of Patents and Trademarks